US012558025B2

(12) United States Patent
Muthuraman et al.

(10) Patent No.: US 12,558,025 B2
(45) Date of Patent: Feb. 24, 2026

(54) METHOD FOR CLASSIFYING A POLYSOMNOGRAPHY RECORDING INTO DEFINED SLEEP STAGES

(71) Applicant: Universitätsmedizin der Johannes Gutenberg-Universität Mainz, Mainz (DE)

(72) Inventors: Muthuraman Muthuraman, Freimersheim (DE); Haralampos Gouveris, Mainz (DE); Philipp Tjarko Boekstegers, Mainz (DE)

(73) Assignee: Universitätsmedizin der Johannes Gutenberg-Universität Mainz, Mainz (DE)

( * ) Notice: Subject to any disclaimer, the term of this patent is extended or adjusted under 35 U.S.C. 154(b) by 734 days.

(21) Appl. No.: 17/440,057

(22) PCT Filed: Mar. 10, 2020

(86) PCT No.: PCT/EP2020/056326
§ 371 (c)(1),
(2) Date: Sep. 16, 2021

(87) PCT Pub. No.: WO2020/193116
PCT Pub. Date: Oct. 1, 2020

(65) Prior Publication Data
US 2022/0183619 A1     Jun. 16, 2022

(30) Foreign Application Priority Data
Mar. 26, 2019     (DE) .......................... 102019107666.8

(51) Int. Cl.
*A61B 5/00*          (2006.01)
*A61B 5/0205*        (2006.01)

*A61B 5/024*         (2006.01)
*A61B 5/087*         (2006.01)
*A61B 5/11*          (2006.01)
(Continued)

(52) U.S. Cl.
CPC .......... *A61B 5/4812* (2013.01); *A61B 5/0205* (2013.01); *A61B 5/02405* (2013.01); *A61B 5/087* (2013.01); *A61B 5/1114* (2013.01); *A61B 5/369* (2021.01); *A61B 5/7267* (2013.01); *G16H 50/70* (2018.01)

(58) Field of Classification Search
None
See application file for complete search history.

(56) References Cited

U.S. PATENT DOCUMENTS

2014/0371547 A1     12/2014   Gartenberg et al.
2015/0190086 A1*     7/2015   Chan .................... A61B 5/4812
                                                              600/300

FOREIGN PATENT DOCUMENTS

CN            107495962 B   *   5/2020   ......... A61B 5/04012
WO        WO2010140117          12/2010
WO        WO-2019018400 A1 *    1/2019   ......... A61B 5/02108

OTHER PUBLICATIONS

Teresa et al. "Sleep Stage Classification with Cross Frequency Coupling". 36th Annual International Conference of the IEEE Engineering in Medicine and Biology Society. (Year: 2014).*
(Continued)

*Primary Examiner* — Sana Sahand
(74) *Attorney, Agent, or Firm* — McHale & Slavin, P.A.

(57) ABSTRACT
A method for classifying or categorizing a polysomnography recording into defined sleep tags.

13 Claims, 5 Drawing Sheets

(51) Int. Cl.
    *A61B 5/369*        (2021.01)
    *G16H 50/70*      (2018.01)

(56)               References Cited

OTHER PUBLICATIONS

Meltzer, L. et al., "Comparison of actigraphy immobility rules with polysomnographic sleep onset latency in children and adolescents", Sleep Breath, vol. 19(4), pp. 1415-1423, doi: 10.1007/s11325-015-1138-6, (Feb. 2015).

Mack, D. et al., "Sleep assessment using a passive ballistocardiography-based system: preliminary validation", 31st Ann. Intl. Conf. of the IEEE Engineering in Medicine and Biology Society: Engineering the Future of Biomedicine, EMBC 2009, pp. 4319-4322, XP031881948, (Sep. 2009).

Roeder, N. et al., "Abstracts der 25. Jahrestagung der Deutschen Gesellschaft fur Schlafforschung und Schlafmedizin e. V.", Somnologie, Springer Medizin Verlag GmbH, vol. 21(Suppl. 2), pp. s45-s138, doi: https://doi.org/10.1007/s11818-017-0140-6, (2017).

Espiritu, H. et al., "Automated detection of sleep disorder-related events from polysomnographic data", 2015 Intl. Conf. on Healthcare Informatics, EEE Computer Society, pp. 1-8, doi: 10.1109/ICHI.2015.105, (2015).

Gouveris, H. et al., "Sleep stage classification using spectral analysis and support vector machine algorithm on C3- and C4-EEG signals", Sleep Machine / Absracts, vol. 40, p. e3-e185, (2017).

Devot, S. et al., "Sleep/wake detection based on cardiorespiratory signals and actigraphy", Ann. Intl. Conf. of the IEEE Engineering in Med. and Biol. Soc., pp. 5089-5092, doi: 10.1109/embs.2010.5626208, (Jan. 2010).

Fonseca, P. et al., "Sleep stage classification with ECG and respiratory effort", Physiological Measurement, vol. 36, pp. 2027-2040, (2015).

Hall, M., "Correlation-based feature selection for machine learning", Dept. of Computer Science, Univ. of Waikato, New Zealand, (1999).

* cited by examiner

METHOD FOR CLASSIFYING A POLYSOMNOGRAPHY RECORDING INTO DEFINED SLEEP STAGES

CROSS REFERENCE TO RELATED APPLICATIONS

This is a national stage filing in accordance with 35 U.S.C. § 371 of PCT/EP2020/056326, filed Mar. 10, 2020, which claims the benefit of the priority of German Patent Application No. 102019107666.8, filed Mar. 26, 2019, the contents of each are incorporated herein by reference.

TECHNICAL AREA

The present invention relates to a method for classifying sleep stages based on a polysomnography recording. More particularly, the present invention relates to a method for classifying or categorizing a cardiorespiratory polysomnography recording into defined sleep stages.

STATE OF THE ART

There are a large number of people who suffer from sleep disorders. Some of the sleep disorders are of a very different nature and can therefore have a variety of different causes.

It is well known that polysomnography recordings can provide clues to the causes of sleep disorders. Polysomnography records a variety of body function data from a patient during the sleep process. In particular, causes of sleep disorders can be identified from the progression of brain waves in specific areas of the brain, cardiac activity, and respiratory intensity and frequency during sleep. Therefore, during a polysomnography, the brain waves at different locations of the brain are recorded by means of an electroencephalography (EEG) and the cardiac activity is recorded by means of an electrocardiography (ECG). In addition, respiratory parameters and, if necessary, snoring sounds are recorded with the aid of a microphone, or electrical muscle activity is measured by means of electromyography (EMG).

Usually, polysomnography is performed in a specially equipped sleep laboratory.

It is further known that sleep can be divided into different sleep stages. Usually, sleep is divided into five different stages, namely stage N1, stage N2 and stage N3 (as parts of non-REM sleep), REM stage, and awake stage, said awake stage corresponding to the epochs or period during sleep when the person is in the awake state. Physical activity respectively data on physical functions differ throughout these stages. This is noticeable, for example, in the fact that the brain waves, which are recorded by means of electroencephalography (EEG), are different in the individual stages. Among other things, both the frequency and the intensity of the brain waves differ. Cardiac activity, in particular the heart rate, also changes from one sleep stage to the next.

In a healthy person, the sleep stages proceed in a more or less regular pattern, in patients with sleep disorders, this pattern may differ from that of a healthy person. In addition, depending on the absolute or percentage sleep stage classification during sleep, various bodily functions may deviate from those of a healthy person.

In order to find the cause of sleep disorders, it is therefore helpful to recognize the individual sleep stages of a patient and to assign bodily functions to certain sleep stages. The causes of a sleep disorder can be identified or narrowed down on the basis of deviations found in the temporal sequence of the steep stages and on the basis of deviations in individual bodily functions in the various sleep stages compared to a healthy person.

A polysomnography recording usually lasts seven to eight hours, as this is the usual duration of a person's sleep. Since some sleep disorders can last only a few seconds, the data are recorded at very short intervals, i.e. quasi continuously.

Due to the large amount of data, it goes without saying that the evaluation of such a polysomnography recording is very time-consuming. Just for the classification of the sleep stages of a polysomnography recording of one complete night, a specialist needs about one to two hours, with sleep being divided into 30 second units, so-called epochs, wherein each epoch is assigned to a sleep stage. Furthermore, the quality of the classification depends on the experience of the specialist.

Attempts have been made to classify a polysomnography recording automatically. However, no satisfactory method has yet been found to automatically classify a polysomnography recording into different sleep stages.

DESCRIPTION OF THE INVENTION

It is the object of the present invention to provide a method for the classification of sleep stages in a polysomnography recording, which can be performed in a time-saving and cost-effective manner.

According to the invention, the object is solved by a method for classifying a polysomnography recording according to claim 1, which comprises the following steps:

First, the sleep of a human being is classified into different sleep stages, wherein the sleep stages are identifiable by means of at least one datatype of the first kind. Then, a plurality of information regarding bodily functions is collected over a predetermined period of time in the form of data, with the data comprising at least one dataset of the datatype of the first kind. The collected data is subdivided into time-dependent data blocks. This may be done manually, i.e. by a person, or automatically by a computer or the like. Subsequently, a limited number of training data blocks are manually selected from the data blocks and assigned to sleep stages, wherein the training data blocks are selected in such a way that the data contained in the training data block can each be uniquely assigned to a defined sleep stage. Preferably, this selection is performed by a trained person or by a specialist. Each dataset of the first kind of each training data block is evaluated by means of a data preparation procedure. Training objects are created from the evaluated data of each training data block, wherein each training object comprises the datasets of the first kind of a training data block evaluated by means of the data preparation procedure and the assignment of the training data block to a sleep stage. The training objects are then transmitted to a support vector machine for creating a classification in the support vector machine. Thereafter, at least some of the data blocks, preferably all data blocks that were not selected as training data blocks, are transmitted to the support vector machine and an automatic classification of these data blocks into the known sleep stages is performed based on the data of the first kind datatype of each data block.

In the context of the invention, the method step of evaluating the dataset of the first kind of each training data block by means of a data preparation procedure is understood to mean both operations namely processing and/or analyzing datasets.

Using the described method, it is possible to perform the larger part of the classification of a polysomnography recording into sleep stages automatically.

However, even if the method is only a partially automated method for classifying polysomnography recordings, only a very small amount of time is required for a specialist or trained person to perform the classification. The classification can thus be performed much more cost-effectively than before.

Surprisingly, it was found that a classification performed by means of the described method has a comparatively high accuracy if the dataset of the first kind includes data regarding the following bodily functions: brain waves, cardiac activity, air flow of respiration, breathing sounds, especially snoring sounds, eye movement patterns, electrical muscle activity in the chin area as well as on the lower leg (Musculus tibialis anterior).

Preferably, the described method according to claim 1 uses at least one of the following measuring methods or measuring devices to collect the dataset of the first kind: electroencephalography, electrocardiography, microphone, air flow meter.

The invention is based on the knowledge that brain waves measured by means of electroencephalography allow particularly good conclusions to be drawn about the sleep stage present in a block of data. In particular, the C3/C4 data of the electroencephalogram are comparatively easy to collect and, due to their symmetrical arrangement on the head of a person, furthermore enable a comparison of the measurement results with each other. Therefore, according to a preferred embodiment of the described method, it is provided that the dataset of the first kind comprises data of an electroencephalography, in particular C3/C4 data of an electroencephalography.

In preferred embodiments of the described method, a good classification of the polysomnography is recording into sleep stages could be achieved by means of the following data preparation procedures: cross-frequency coupling, entropy method, power spectral analysis and determination of head rate variability when the dataset of the first kind includes cardiac function data.

Furthermore, the invention is based on the knowledge that the data recorded by means of an electroencephalogram result from a superposition of several oscillating signals. The electroencephalogram thus captures different frequency components that interact with each other. Classical analyses of power frequency, based for example on the fast Fourier transform (FFT) or various transforms of time (e.g. Hilbert transform), represent modulations of amplitudes within a defined frequency per time. However, they cannot identify the relationships of different frequencies or frequency components to each other. By means of cross frequency coupling (CFC), it is possible to synthesize coupling frequencies. The use of the cross frequency coupling method enables a support vector machine to correctly classify comparable data with a high degree of certainty. Among the various cross-frequency coupling methods, phase-amplitude coupling has been particularly useful. According to a preferred further development, the step of evaluating the dataset of the first kind of each training data block by means of a data preparation procedure thus comprises cross-frequency coupling comprising a phase-amplitude coupling. This phase-amplitude coupling can be used to classify the data of an electroencephalogram into sleep stages with particular accuracy.

With regard to the evaluation of a polysomnography recording, it is advantageous that the recorded data are divided into a predefined time interval, wherein in particular the time interval is in the range of 15 seconds to 5 minutes and, in particular with regard to electroencephalographic signals, is preferably 30 seconds (so-called 30-second epoch).

In a preferred embodiment of the method, two to six, preferably four, training data blocks are selected for each defined sleep stage.

In order to accurately evaluate the large number of data blocks available in a short period of time, it is advantageous for the support vector machine to comprise an algorithm that uses a non-linear basis kernel function.

In a first embodiment of the method, the data on the bodily functions are collected in a sleep laboratory, wherein the data on the bodily functions are collected preferably during the second night in the sleep laboratory.

Alternatively, the data on the bodily functions can be collected in a home environment.

A very high match rate respectively a very high hit rate in the classification of sleep stages according to the described method can be achieved if the dataset of the datatype of the first kind consists of the data of an electroencephalography, in particular of C3/C4 data of an electroencephalography, and if the evaluation of the dataset of the first kind of each training data block is performed by means of cross-frequency coupling with a phase-amplitude coupling.

Also in a method in which the dataset of the datatype of the first kind consists of the data of an electroencephalography, in particular of C3/C4 data of an electroencephalography, and in which the evaluation of the dataset of the first kind of each training data block is performed by means of a power spectral analysis, high match rates in the classification of sleep stages could be achieved.

This also applies to methods in which the dataset of the datatype of the first kind consists of at least one of the following datatypes: data of an electroencephalography, in particular C3/C4 data of an electroencephalography, respiratory flow, snoring sounds and in which the evaluation of the dataset of the first kind of each training data block is performed by means of an entropy method.

Finally, a method in which the dataset of the datatype the first kind consists of the data of an electrocardiography and in which the data preparation procedure comprises a procedure to determine the heart rate variability has also proven to be effective.

BRIEF DESCRIPTION OF THE DRAWINGS

Preferred embodiments are explained in more detail with reference to the accompanying drawings, in which.

BEST WAY TO CARRY OUT THE INVENTION

Figure 1:
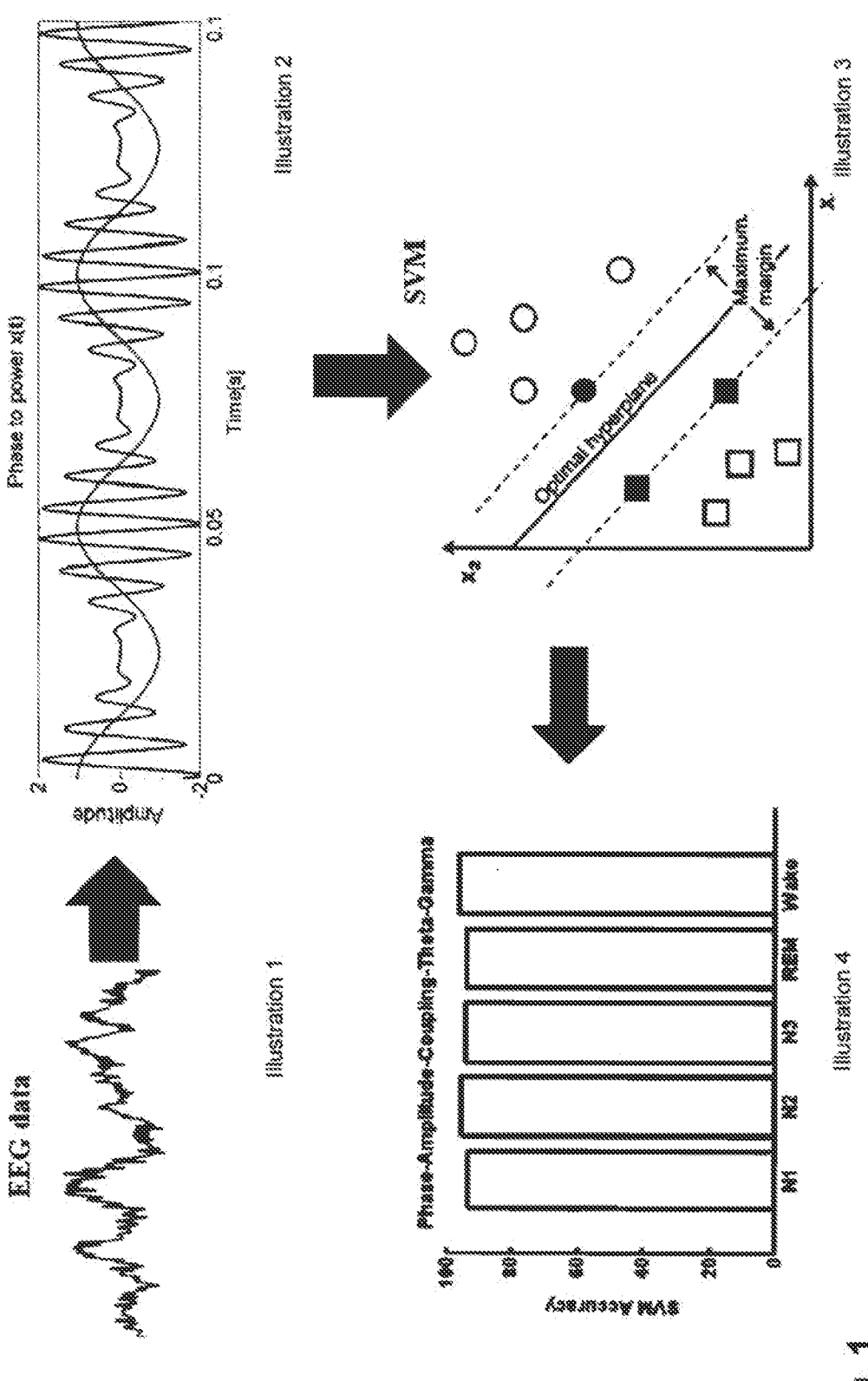
FIG. 1 shows a schematic representation of the flow of a method for classifying a polysomnography recording into defined sleep stages using electroencephalography (EEG) data in conjunction with a frequency coupling method.

FIG. 1 shows a schematic representation of the flow of a method for classifying a polysomnography recording into defined sleep stages based on electroencephalography (EEG) data in conjunction with a frequency coupling method.

In the first step of the method shown in FIG. 1, a person's sleep is divided into different sleep stages. Usually, sleep is divided into the five known stages, namely stage N1, stage N2, stage N3, REM stage and awake stage.

Each of these known stages can be identified on the basis of at least one datatype of the first kind. In the specific case, it is intended to automatically identify and classify the individual stages on the basis of the brain waves recorded by means of electroencephalography.

The next step is collecting a plurality of information regarding bodily functions during a person's sleep in the form of a well-known polysomnography recording in a sleep laboratory. Typically, a polysomnography recording lasts seven to eight hours.

The collected data is divided into time-dependent data blocks with a duration of 30 seconds. This can be done manually, i.e. by a person, or automatically by a computer or the like.

From said data blocks, a trained person or a specialist selects a limited number of training data blocks and assigns each of these selected training data blocks to a sleep stage, wherein the trained person or the specialist selects the training data blocks in such a way that the data contained in the training block can each be uniquely assigned to a defined sleep stage. Ideally, the trained person or specialist selects the same number of training data blocks for each sleep stage. It has been shown that the selection of four training data blocks per sleep stage is sufficient. However, it goes without saying that more or fewer training data blocks can be selected within the scope of the described method.

The polysomnography recording and thus the data blocks contain, among other things, the brain waves recorded by means of electroencephalography. The brain waves were recorded at different locations in the brain. For the further procedure of classifying a polysomnography recording into sleep stages, the data recorded at positions C3 and C4 on the head of a patient by means of electroencephalography are used (see illustration 1 in FIG. 1). Positions C3, C4 are those positions commonly referred to as C3, C4 in electroencephalography.

The data of each training data block obtained at the C3/C4 positions of an electroencephalography are analyzed using a data preparation procedure.

It is known that the frequency and amplitude of brain waves change during the different sleep stages. Each sleep stage is characterized by the presence respectively intensity or amplitude of different known frequency groups. Thus, the data displayed by the electroencephalogram at one position of the brain represent a superposition of different signals emitted by the brain in the form of brain waves. A simple frequency analysis of the collected data, for example in the form of a fast Fourier transform, due to the superimposed signals does not provide frequency sequences that can be clearly assigned to a steep stage.

For this reason, the data obtained at the C3/C4 positions of the electroencephalography are processed using cross-frequency coupling (see illustration 2 in FIG. 1). Surprisingly, it has been found that a cross-frequency coupling method with a phase-to-amplitude method is particularly suitable for assigning sleep stages to the data of an electroencephalogram.

From the data collected in the course of electroencephalography, two frequency groups are identified at the C3/C4 positions, the course and intensity of which can be described precisely by means of phase-to-amplitude coupling. By means of phase-to-amplitude coupling, the dependence between the amplitude of a higher-frequency signal and the phase of a lower-frequency signal is represented. The characteristic course of the frequency groups processed by means of phase-to-amplitude coupling can be clearly assigned to a seep stage.

The data of a data block obtained by means of cross-frequency coupling, in particular by means of phase-to-amplitude coupling, are correlated with the sleep stage determined by a skilled person and thus form a training object.

The training objects obtained from the selected data blocks are transmitted to a support vector machine to create a classification in the support vector machine (see Illustration 3 in FIG. 1).

An algorithm included in the support vector machine marks each data element as a point in n-dimensional space, where n represents the number of features. The algorithm has to calculate the best mean value between different separating straight lines in order to find the best common separating plane for a points, in this case a line with the maximum possible distance to all data points. The classification is performed by determining the so-called optimal hyperplane. As a next step, the algorithm looks for the hyperplane on which those data points with the smallest distance to said optimal hyperplane are located, the so-called support vectors. This distance is given the name Margin. The optimal separating hyperplane now maximizes the Margin to obtain clearly separated classification groups. The support vector machine thus divides the training data blocks into the specified sleep stages.

Then, the remaining data blocks that were not selected as training data blocks are transmitted to the support vector machine and an automatic classification of these data blocks into the known sleep stages based on the C3/C4 data of an electroencephalography is performed.

In a test phase, the described method was able to correctly assign the data blocks to sleep stages and thus achieve a hit rate of more than 93% (see Illustration 4 of FIG. 1).

A particularly accurate classification of data blocks which are not selected as training data blocks is achieved by using a non-linear basis kernel function in the support vector machine algorithm.

Figure 2:
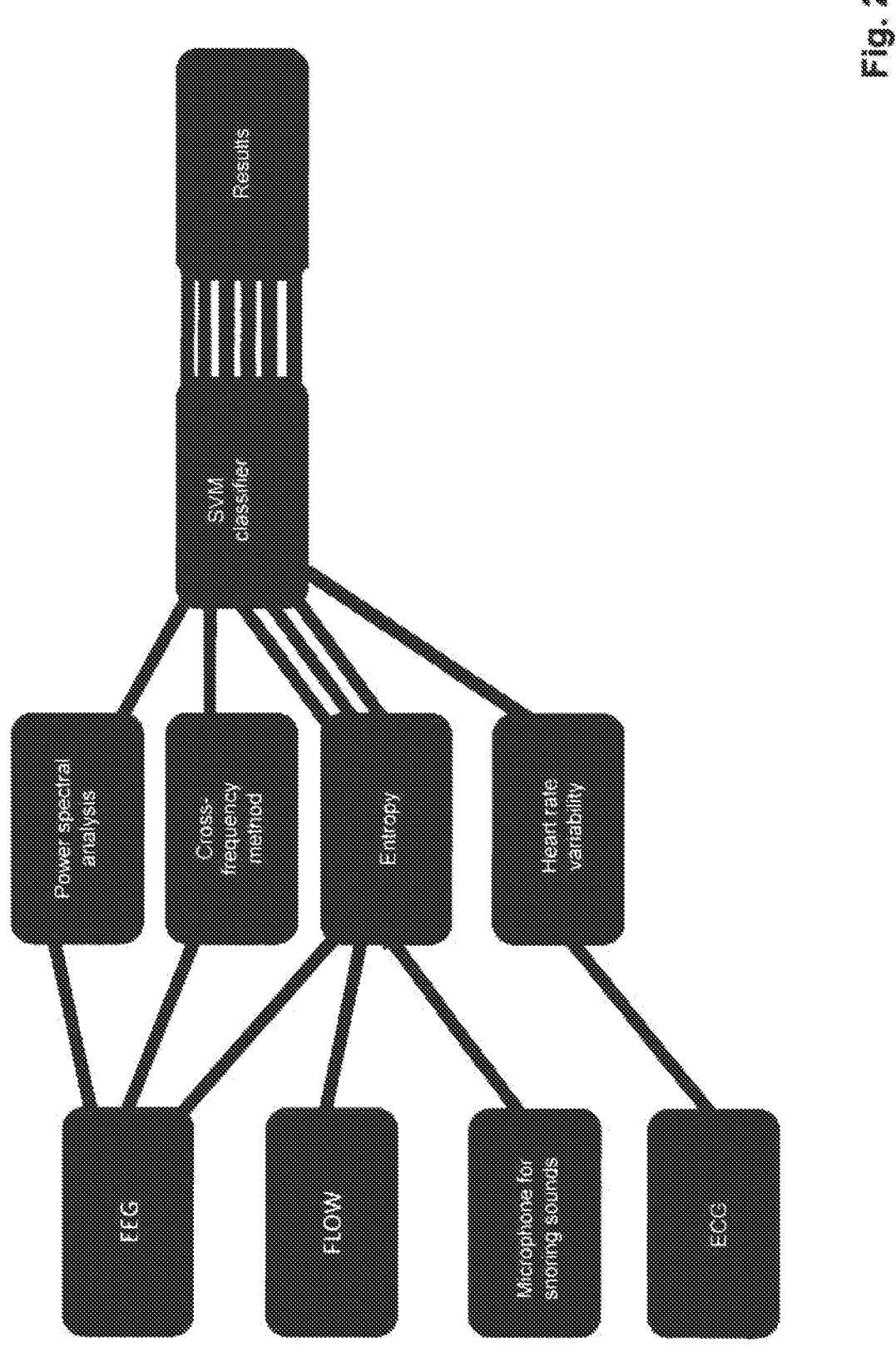
FIG. 2 shows an overview of the usable data of the first kind and corresponding data processing methods.

FIG. 2 shows an overview of the first kind of data that can be used in the present method and that are suitable for performing a classification, and corresponding data preparation procedures for evaluating, the first kind of data.

Instead of the data of an electroencephalography as used in connection with FIG. 1, the data of the respiratory flew, the data of the snoring and the data of an electrocardiography are also suitable as data of the first kind for carrying out the described method if suitable data preparation procedures are used.

Thus, as an alternative to the cross-frequency method used in connection with FIG. 1, the data of the first kind can also be evaluated by means of a power spectral analysis or an entropy method.

Figure 3:
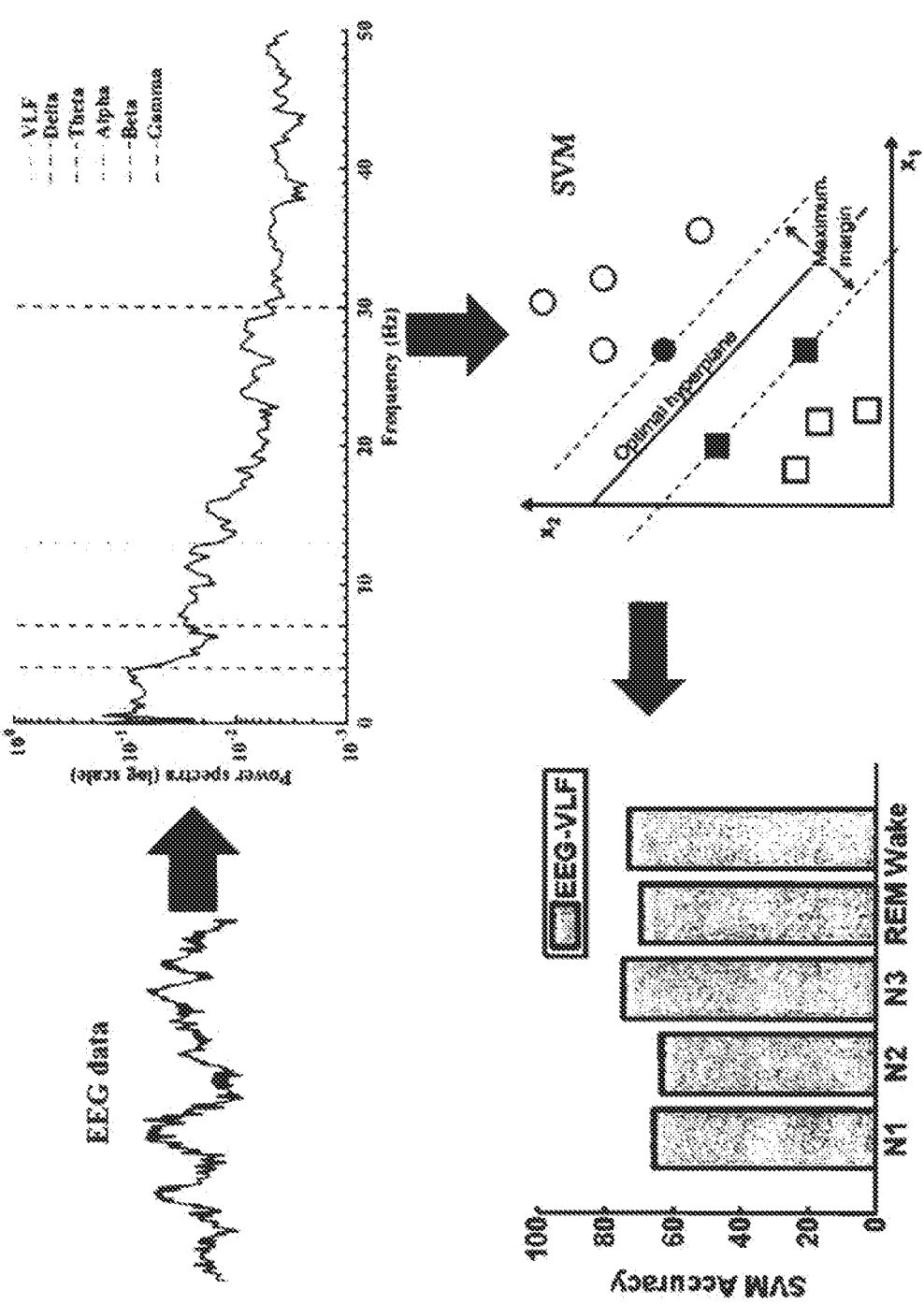
FIG. 3 shows a schematic representation of the flow of a method for classifying a polysomnography recording into defined sleep stages using electroencephalography (EEG) data in conjunction with power spectral analysis.

In power spectral analysis, the frequency-related power of a signal in a frequency band is specified. Power spectral analysis is suitable, for example, for data from an electroencephalography (see FIG. 3). In particular, the multi-taper method is suitable for this purpose.

As already mentioned above, classical frequency transformations such as the Fourier transform can only be applied to electroencephalography data insufficiently or not at all For example, a Fourier transform lacks the time-related reference to the respective frequencies. The multi-taper method generates such a time-frequency representation by multiplication in the frequency domain.

The entropy method is a non-linear dynamic analysis. The main principle of entropy methods is the quantification of information of a signal and of the probability of occurrence of certain patterns within a finite number of patterns and within a time series of the signal. The more information conveyed within a signal, the higher the entropy of the signal. While there are several kinds of entropy methods, in the context of sleep stage classification, the sample entropy method is particularly suitable, which is a modification of the approximate entropy method.

In the approximate entropy method, time series are examined regarding similar epochs, with more frequent and more similar epochs leading to lower values of approximate entropy. Thus, lower values of approximate entropy signify a high level of regularity of the signal and, conversely, high values of approximate entropy signify an irregular signal.

However, the approximate entropy method is dependent on the dataset length. Thus, in order to avoid the results being dependent on dataset length, an entropy method is used in which sequences that agree with themselves are not counted and which functions independently of dataset length. Said entropy method is the sample entropy method mentioned above, which is a modification of the approximate entropy method. The sample entropy method also has the advantage of being faster to perform.

Figure 4:
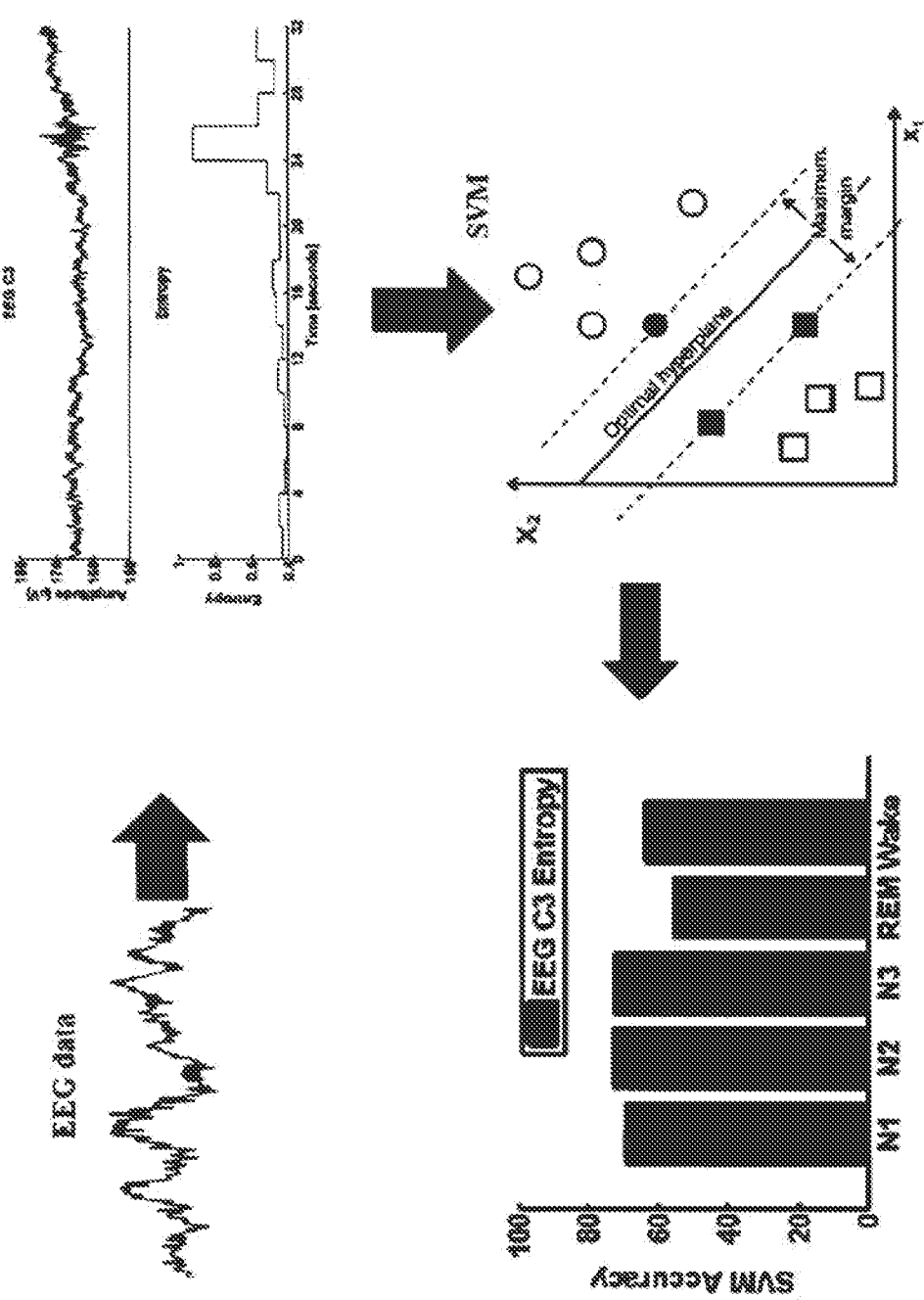
FIG. 4 shows a schematic representation of the flow of a method for classifying a polysomnography recording into defined sleep stages using electroencephalography (EEG) data in conjunction with an entropy method.

It is particularly advantageous to use the sample entropy method in conjunction with electroencephalography data, as shown in FIG. 4. Respiratory flow and snoring data can also be used for this method.

Figure 5:
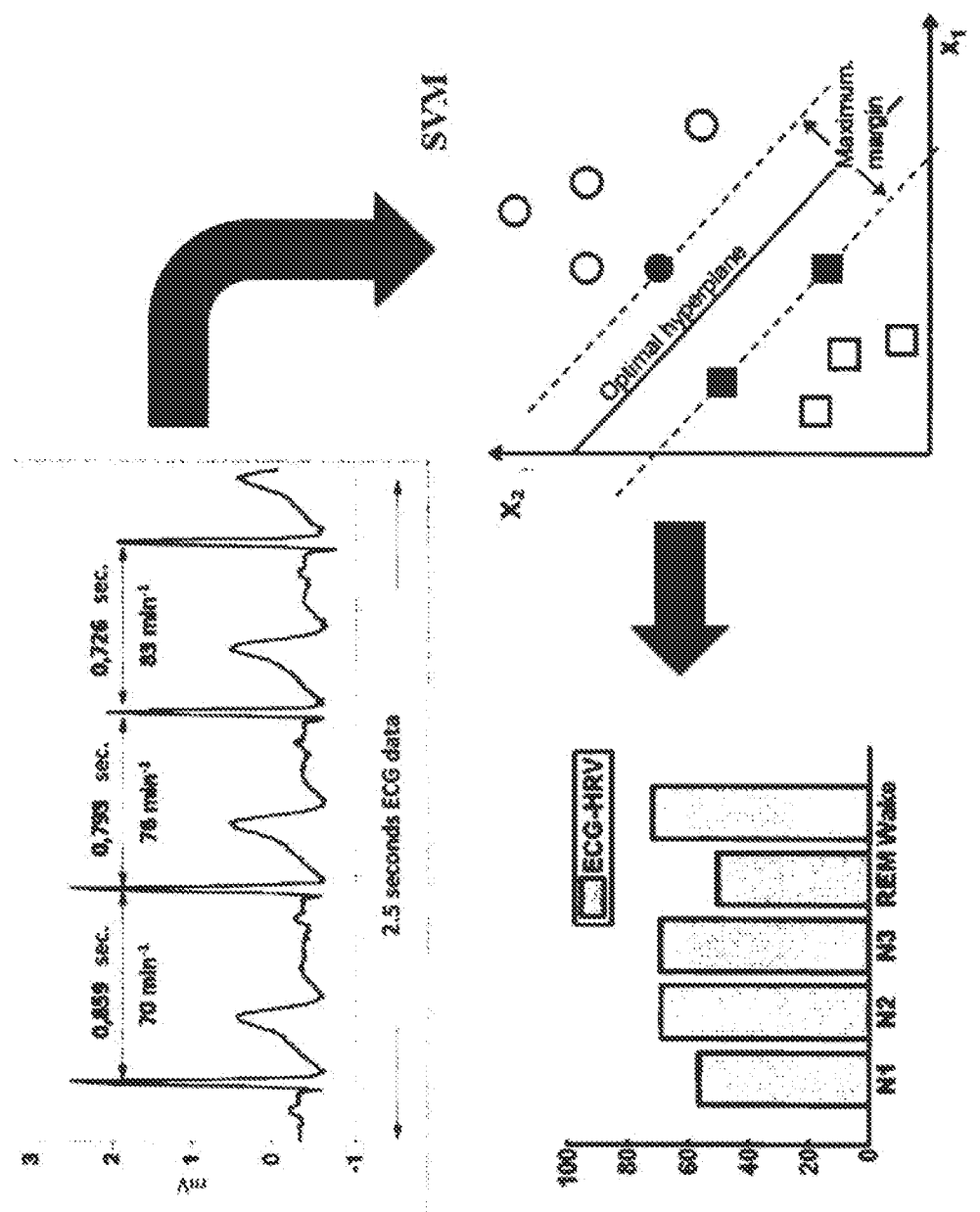
FIG. 5 shows a schematic representation of the flow of a method for classifying a polysomnography recording into defined sleep stages using electrocardiography (ECG) data in conjunction with the determination of heart rate variability.

In the event that the data is taken from an electrocardiography, a data preparation procedure that determines heart rate variability from the collected data is also suitable (see FIG. 5).

The interval between two heartbeats is usually defined as the time between the onsets of two contractions of the heart chambers. This onset of ventricular contraction is shown in the electrocardiogram as an R-wave, and the interval between two R-waves is called the RR-interval. The RR-intervals are usually not of equal length, but are subject to fluctuations. The quantification of these fluctuations is called heart rate variability (HRV).

The heart rate variability of a selected training data block determined from the data of an electrocardiography, together with the assignment to the sleep stage, already serves as a training object which can be transmitted to the support vector machine. The data blocks which are not selected as training data blocks can be classified into sleep stages by the support vector machine on the basis of the heart rate variability.

Even though in the described method the best hit rate respectively the best assignment of data blocks to sleep stages was achieved with the C3/C4 data using a cross-frequency method, a satisfactory hit rate was also achieved with the procedures using the entropy method or power spectral analysis. Except for the procedure using the snoring sounds as the first kind of data, the hit rates ware generally above 50%, in some cases well above 50%.

Heart rate variability is also suitable for the classification of sleep stages by means of the described method, Here, too, the hit rates are above 50%.

The invention claimed is:

1. A method for finding the causes of sleep disorders by comparing collected bodily function data of an individual with given bodily function data of a healthy person in a certain sleep stage wherein the method for finding the causes of sleep disorders comprises a method for classifying a polysomnography recording into defined sleep stages with the following steps:

classifying the sleep of a human being into different sleep stages, wherein the sleep stages are identifiable by means of at least one datatype of a first kind;

carrying out a polysomnography and collecting a plurality of information regarding bodily functions over a predetermined period of time in the form of data, with the data comprising at least one dataset of the datatype of the first kind;

wherein for collecting the datatype of the first kind an electroencephalography is used and the dataset of the first kind comprises C3/C4 data of an electroencephalography, subdividing the collected data into time-dependent data blocks manually or automatically;

manually selecting a limited number of training data blocks from the data blocks and assigning them to a sleep stage, wherein the training data blocks are selected in such a way that the data contained in the training block can each be uniquely assigned to a defined sleep stage;

evaluating the C3/C4 data of the dataset of the first kind of each training data block by means of a data preparation procedure comprising a cross-frequency coupling method;

creating training objects, wherein each training object comprises the datasets of the first kind of a training data block evaluated by means of the data preparation procedure comprising the cross-frequency coupling method and the assignment of the training data block to a sleep stage;

transmitting the training objects to a support vector machine for creating a classification;

transmitting at least some of the data blocks that were not selected as training data blocks to the support vector machine and automatically classifying said data blocks into the known sleep stages based on the data of the datatype of the first kind of the data blocks.

2. The method according to claim 1, characterized in that the data collected in the polysomnography comprises data of the following bodily functions: brain waves, cardiac activity, air flow of respiration, breathing sounds, in particular snoring sounds, eye movement patterns, electrical muscle activity in the chin area and on the lower leg.

3. The method according to claim 2, characterized in that data of bodily functions collected in the polysomnography axe correlated with corresponding sleep stages and in that data of bodily functions in a certain sleep stage are compared with existing data of bodily functions collected from healthy persons having been in the same sleep stage.

4. The method according to claim 1, characterized in that the cross-frequency coupling method comprises a phase-amplitude coupling.

5. The method according to claim 1, characterized in that the collected data are divided into a predefined time interval, wherein in particular the time interval is in the range of 15 seconds to 5 minutes.

6. The method according to claim 5, wherein the time interval is 30 seconds.

7. The method according to claim 1, characterized in that two to six training data blocks are selected for each defined sleep stage.

8. The method. according to claim 7, characterized in that four training data blocks are selected for each defined sleep stage.

9. The method according to claim 1, characterized in that the support vector machine comprises an algorithm that uses a non-linear basis kernel function.

10. The method according to claim 1, characterized in that the data on the bodily functions are collected in a sleep laboratory.

11. The method according to claim 1, characterized in that the data on the bodily functions are collected in a home environment.

12. The method according to claim 1, characterized in that the dataset of the datatype of the first kind consists of the data of an electroencephalography, and in that the evaluation of the dataset of the first kind of each training data block is performed by means of cross-frequency coupling with a phase-amplitude coupling.

13. The method according to claim 1, characterized in that the data on the bodily functions are collected during the second night in the sleep laboratory.

* * * * *